United States Patent [19]

Cornaby et al.

[11] Patent Number: 4,959,302
[45] Date of Patent: Sep. 25, 1990

[54] METHOD OF EVALUATING IMMUNE SYSTEM RESPONSE TO ALLOGRAFTS, VIRAL INFECTION AND IMMUNOSUPPRESSIVE THERAPY

[75] Inventors: Andrew J. Cornaby, Boston; Roy A. Dempsey, Cambridge, both of Mass.

[73] Assignee: Endogen, Inc., Boston, Mass.

[21] Appl. No.: 87,630

[22] Filed: Aug. 20, 1987

[51] Int. Cl.$^5$ .................. G01N 33/543; G01N 33/569
[52] U.S. Cl. ............................................. 435/5; 435/7;
435/29; 436/87; 436/518; 436/536; 436/811
[58] Field of Search ................. 436/87, 501, 518, 811,
436/815, 536; 435/29, 948, 5, 7

[56] References Cited

U.S. PATENT DOCUMENTS 4,707,443 11/1987 Nelson et al. ..................... 935/110

FOREIGN PATENT DOCUMENTS 0102601 3/1984 European Pat. Off. .
3628718 6/1987 Fed. Rep. of Germany .
8705912 10/1987 PCT Int'l Appl. .

OTHER PUBLICATIONS

Abbud-Filmo et al, *Journ. Immunol.*, 133, 2582–2586, 1984.
Attallah et al, Int. Archs. Allergy Appl. Immun., 84, 10–17, 1987.
Charpentier et al, *Transplant. Proc.*, 19, 1572–1573, 1987.
Vie et al, *Kidney Int.*, 26, 658, 1984.
Vie et al, *Biol. Abstr.*, 81, Abstr. No. 4506, 1986.
Walters et al, *Fed. Proc.*, 46, 1365, 1987.
Yamaguchi et al, *Fed. Proc.*, 45, 995, 1986.
Kimball, *Introduction to Immunology*, MacMillan Publishing Co., Inc., New York, 1983, pp. 215–222 and 475–477.
Colvin et al, *Biol. Abstr.* 84, Abstr. No. 36243, 1987.
Peacocke et al, *Clin. Res.*, 34, 605A, 1986.
Lawrence et al, *Chest*, 69, (6 Suppl.), 5265, 1986.
Southern et al, *Lab. Invest.*, 56, 75A Abstr. No. 445, 1987.
Southern et al, *J. Heart Transplant.*, 5, (No. 5), 370, Abstr. No. 29, 1987.

Primary Examiner—Esther L. Kepplinger
Assistant Examiner—David A. Saunders
Attorney, Agent, or Firm—Hamilton, Brook, Smith & Reynolds

[57] ABSTRACT

Detection of solublen Interleukin-2 (IL-2) and Interleukin-2 receptor (IL-2R) levels in the serum, plasma, urine and bile of kidney and liver transplant patients using sensitive immunoassays provides valuable prognostic, monitoring and diagnostic information about impending, acute and chronic or recovering allograft rejection episodes. Additionally, monitoring immune system activation with these sensitive immunoassays can be useful for detecting viral and other infections and for distinguishing cyclosporine toxicity from graft rejection.

22 Claims, 6 Drawing Sheets

METHOD OF EVALUATING IMMUNE SYSTEM RESPONSE TO ALLOGRAFTS, VIRAL INFECTION AND IMMUNOSUPPRESSIVE THERAPY

BACKGROUND

Clinical organ transplantation has exploded in recent years. According to the registries of the U.S. Department of Health and Human Services and the European Dialysis and Transplantation Association, 7,000 renal transplants were performed in the U.S. and 17,000 were performed worldwide in 1984. The statistics for 1986 are estimated to show that 22,000 kidney transplants were performed throughout the world. In 1986 it is estimated that 900 liver transplants were performed worldwide.

It is now estimated that the number of kidney transplants is increasing by 15 to 20 percent annually worldwide, while liver, heart, heart/lung, bone marrow, and pancreas are increasing by approximately 30–60% annually as more organ transplant centers open up worldwide.

The introduction of the fungal cyclic peptide metabolite Cyclosporine (CsA) has been one of the most important therapeuticdevelopments in the managements of patients receiving organ allografts. While allowing for a great deal of success, immunosuppressive drugs have numerous side effects, in some cases so severe that they lead to the patient's death. The clinical challenge in organ transplantation lies in balancing the immunosuppressive effects on these drugs against their side effects. If too little immunosuppression is given, rejection of the allograft may occur, whereas too much may lead to life threatening infections and an increased incidence of malignancy as the body's normal defenses against malignancy are suppressed. Organ transplantation could be performed with much greater frequency if there were available better methods to monitor and control the body's exquisitely sensitive system of recognizing and rejecting foreign tissues.

Allograft rejection may be defined as the immunologic response to foreign tissues, which leads to loss of function of the graft and to its eventual destruction by immunocompetent cells. Rejection is easy to define but can be very difficult to diagnose in clinical practice. The principle diagnostic procedures presently available monitor organ function. These tests provide indication of decreased function of the transplanted organ, but not of rejection directly. An organ biopsy can determine more precisely whether organ disfunction is due to the onset of graft rejection or other factors such as immunosuppressive drug toxicity or infection. Typically, a physician will only decide to perform a biopsy once abnormal organ function tests have been detected.

RENAL TRANSPLANTATION

Serum creatinine is the test most commonly used to detect renal allograft rejection and has been used for that purpose since the inception of renal transplantation. Rejection is considered when the serum creatinine level rises 0.5 mg/dl or by 25%. Smaller increases may indicate rejection in children. Serum creatinine levels, however, lack absolute specificity in the detection of renal allograft rejection. A variety of clinical conditions can lead to an elevation of the serum creatinine apart from rejection and these include uretral obstruction, lymphocele, arterial stenosis, infection, recurrence of original disease, hyperglycemia, acute tubular necrosis, and drug toxicity. Certainly a major clinical problem currently is differentiating CsA toxicity from acute rejection.

As rejection occurs and creatinine levels increase, clinical changes may also occur including fever, tenderness over the graft, enlargement of the graft and decreased urine output. A problem with diagnosing rejection by an elevation of the serum creatinine and other routine laboratory tests, as well as clinical changes, is that rejection has already progressed sufficiently to cause significant renal injury. For this reason, investigators have been searching for years for a means to detect rejection at its earliest stage so that anti-rejection treatment can be initiated early, the rejection episode aborted and permanent renal injury prevented.

Numerous tests have been proposed in the past to detect rejection before the serum creatinine becomes elevated, or to differentiate rejection from other causes of an elevated creatinine levels, of which CsA toxicity is the most common clinical problem facing transplant surgeons.

Histological changes consistent with rejection as seen on a biospy specimen have always been the "gold standard" of diagnosing rejection. However, renal biopsy is an invasive procedure with a risk or injury to the renal vessels, hemorrhage, possible kidney loss, and even death. There is also evidence that renal biopsy results may not be totally reliable, and several studies have shown that prospective biopsies do not predict which patients will have a clinical rejection episode. Because of the risks and also because it is a costly procedure, cytologists have analysed fine needle aspiration biopsies, which are less invasive and less costly. However, the interpretation of these biopsies requires a trained cytologist whose skills are not available to most transplant centers.

Immunological monitoring (e.g. spontaneous blastogenesis and mixed leukocyte reaction assays) has been previously tried for assessing the immune status of transplant recipients in the hope of detecting early rejection. While these early immune monitoring studies provided useful information on how groups of transplant recipients behaved immunologically, they were not helpful in making clinical decisions about individual patients. The most obvious reasons were that it took several days before results were available and the clinical event had already become apparent. These tests were also costly and could only be performed at interested research laboratories, and only on selected patients.

The ratio of CD4 (Helper/inducer) to CD8 (Suppressor/cytotoxic) lymphocytes varies with infection and rejection. Although measuring these T-cell surface marker subsets can give useful information, they cannot be performed repeatedly on every recipient at large transplant centers because of the time involved and also because of the high cost. It is also debatable whether the information one obtains using peripheral blood may be relevant to what is happening locally in the kidney. Several other tests for rejection have also been suggested and tried, e.g. $^{131}$I-Fibrinogen uptake by the graft, and Beta$_2$-microglobulin in the urine, yet the serum creatinine still remains the most useful methods of diagnosing rejection at the present time.

Hepatic Transplants

The same problems exist when monitoring liver allograft recipients. In liver allograft rejection, by the time changes have occurred in serum bilirubin or liver function tests (e.g. alkaline-phosphatase, aspartate and alanine transaminase tests) considerable and sometimes irreversible damage to the liver allograft has already occurred. Presently, liver biopsy, serum bilirubin, and serum liver function tests are the predominant means of monitoring liver allograft recipients. CsA is known to be hepatotoxic and at the present time there is no reliable means of differentiating between CsA toxicity and rejection in liver allografts apart from reducing the CsA dose and seeing an improvement in the serum bilirubin and liver function tests.

Infection

A further problem which plagues transplant recipients is the risk of bacterial, viral or fungal infection. Because of the immunosuppressive treatment which transplant patients receive, they are prone to infection, and these, when they occur, can become life threatening. The relationship of viral infection to rejection episodes has been debated for many years. However, there is now evidence that infection with certain viruses, especially cytomegalovirus (CMV), can precipitate a rejection episode. The early detection of viral infection in renal and other allograft recipients would be extremely useful in order to institute appropriate treatment before infection becomes established and becomes life threatening or precipitates a rejection episode.

The indicators of infection presently available to the physician include changes in the white blood cell count, changes in the organ function tests and positive blood or urine cultures. Such methods at the present time do not allow for the early and rapid detection of infection. Testing cultures from blood, urine, or other fluids takes several days to obtain results, and even then has the potential of giving a false negative indication. Additionally, tests based on organ function do not give an indication whether such a decrease is due to infection or to allograft rejection. By the time microbial tests are confirmed, irreparable tissue damage or loss of the organ function may have already occured.

Cyclosporine (CsA) Toxicity

With the arrival of the new immunosuppressive drug Cyclosporine (CsA), came yet another problem in the differential diagnosis of rejection. This drug is potentially toxic to every organ whose rejection it is trying to prevent. The therapeutic range for CsA is very narrow and in addition, patients do not metabolize the drug uniformly and the effective immunosuppressive dose for CsA varies considerably from patient to patient. If insufficient drug is administered, immunosuppression is ineffective and organ rejection generally results: on the other hand, the administration of too much drug may lead to toxicity. This makes the clinical differentiation of rejection from CsA toxicity very difficult. It is extremely difficult to diagnose cyclosporine toxicity by serum or plasma concentrations alone. The treatment for CsA toxicity is to reduce the dose of cyclosporine whereas the treatment of rejection is exactly opposite. See Keon, P. A. and Stiller, C. R. *Hospital Practice* 15:147-160 (1987).

Because both acute rejection and CsA nephrotoxicity or hepatotoxicity occur frequently, it is important to be able to distinguish one from the other. Several methods have been employed to maker these diagnoses, including the use of clinical and laboratory signs, morphologicaly examination, renal subcapsular pressure, blood and plasma CsA concentrations, and immunological monitoring. There is no histological change on biopsy that is unique to CsA toxicity, which makes it difficult to detect rejection from CsA toxicity on a biopsy specimen. Most transplant centers monitor plasma or serum CsA levels daily in the hope of being able to distinguish between CsA toxicity and rejection. The problem here is that some patients have CsA toxicity with unrecordable levels of CsA in their plasma or serum, whereas other patients who do not have CsA toxicity can have very high levels in their plasma or serum. No test at the present time is reliable in differentiating cyclosporine toxicity from acute graft rejection. There are two ways of being certain you are dealing with CsA toxicity. The first is if a reduction in the CsA dose leads to an improvement in the serum creatinine in renal allograft recipients, and in serum bilirubin and liver function tests in liver allograft recipients. The second is if the symptoms or signs of CsA toxicity disappear when the he CsA dose is reduced.

The measurement of successively lower IL-2 and IL-2R levels by the methodologies described herein provides immunological monitoring, and can indicate the success or failure of the specific immunosuppressive agent's effect on immune activation.

Autoimmune Disorders

A major problem of monitoring organ transplants is related to the cytotoxicity which can result from immunosuppressive therapy as has been previously discussed. Immunosuppressive drugs are routinely used in various clinical situations, either to manipulate or suppress the immune system response to foreign tissue, or an autoimmune response to host tissue. Organ or tissue transplantation requires extensive immunsuppressive therapy prior to and during the transplantation process itself. Afterward, patients must be maintained for their entire lifetime on immunosuppressive drugs in order to prevent host rejection of the foreign tissue. Autoimmune diseases such as systemic lupus erythematosis (SLE) and rheumatoid arthritis belong to another category of chronic inflammatory diseases which result from abberations and abnormalities in a patient's immune system wherein the body rejects its own tissue. To minimize the development of systems associated with these diseases, immunosuppressive therapy is also routinely used. Several different types of immunosuppressive drugs have been utilized over the years.

Interleukin 2

IL-2 is a soluble immunomodulatory protein which has been demonstrated to play a central role in the regulation of both cell-mediated and humoral T-cell dependent immune responses. Its roles include the regulation of normal and neoplastic cell growth and immune activation. IL-2 is responsible for T-cell proliferation (Mier, J. and Gallo, R., *Proc. Natl. Acad. Sci.* 77:6134–6138 (1980); Gillis, S. et al. *J. Immunol.*, 120:2027–2031 (1978)) as well as the differentiation of cytolytic T-cells (CTL), lymphokine activated killer cells (LAK) from functionally inert precursors, and the augmentation of natural killer (NK) cell activity. These cytotoxic cells in turn are capable of destroying tumor cells, virus infected cells or foreign grafted tissue.

The contention that IL-2 production is central to the body's ability to mount a cell-mediated immune response is supported by a number of investigations. Defective IL-2 production is a central feature of many congenital and acquired T-cell immunodeficiencies. For instance, IL-2 is not produced in nude mice and the concurrent administration of IL-2 and sensitized cells is required for the induction of specific helper T-cells. In irradiated rats which had received cardiac allografts that functioned in a stable manner for months, administration of IL-2 was followed by graft rejection (Clason, A. E. et al., J. Immunol. 129:252 (1980)) In bone marrow transplant recipients, in vitro IL-2 production was absent or low in 32 of 34 patients at least two years after surgery, implying that IL-2 production is suppressed (Azogui, O. et al., J. Immunol. 131:3,1205–1208 (1983). In patients with systemic lupus erythematosis (SLE), defective production of both IL-2 and IL-2 have been observed and may be important in the pathogenesis of this disorder (Linker-Israel, M. et al., J. Immunol. 130:2651–2655 (1983)). In rheumatoid arthritis patients, an interleukin-2 like activity has been demonstrated in the synovial fluids. Using an IL-2 dependent cell line to measure IL-2 levels, it was found that 71% of rheumatoid synovial fluids contained an IL-2 like activity. Wilkins, J. A. et al., J. Rheuma 10:1,109–113 (1983).

CsA is known to prevent the synthesis of IL-2 in response to T-cell stimuli (Granelli-Piperno, A. et al., J. Exp. Med. 160: 179–1802 (1984). It has been demonstrated that administration of IL-2 restores immune function in animals treated with CsA (Wang, G. S. et al., Transplantation 33:454 1982). Another immunosuppressive agent used to prevent rejection is prednisone, an anti-inflammatory glucocorticoid known to block the synthesis of several cytokines, including IL-2.

The method currently utilized in most laboratories for the quantification of IL-2 levels in plasma, serum, culture supernatants, and other biological fluids remains the original bioassay based on the incorporation of $^3$H-thymidine in cultured murine IL-2 dependent cytolytic T-lymphocytes cytes (CTLL-2) (Gillis, S. et al., J. Immunol. 120:2027–2031, 1978). Though reasonably sensitive, IL-2 bioassays are cumbersome and subject to variability. They take three days or more to complete, use radioactive isotopes, and require the continual maintenance of indicator cell lines in tissue culture. Briefly, indicator cells in the proper growth phase are seeded into polystyrene wells. Standards and samples are incubated for 48 hours at 37° C. The plates are then pulsed with $^3$H-thymidine. After 18–24 hours, cells are harvested and incorporation of the radioisotope mounted using a beta counter. IL-2 levels in samples are extrapolated in relation to the known standards. Unfortunately, growth parameters are subject to unpredictable change over time. Frequently, indicator cell lines proliferate in response to other lymphokines, and they need to be resubcloned to maintain sensitivity and specificity for IL-2.

Bioassays using the murine CTLL-2 line or subsequently developed lines such as the human HT-2 cell line are also known to be affected by substances in serum which alter the proliferative response of murine and human target cells (Lotze, M. et al., J. Immunol. 134:157–166, 1955). Because of such effects, bioassays are plagued by problems of inter-assay reproducibility and intra-assay variability depending largely on the condition of the cells at the time of assay. They are also limited to a narrow range of linearity in the detection of IL-2 (approximately 0.1 unit/ml to 10 unit/ml).

IL-2 Immunoassays

The ability to detect IL-2 utilizing an immunoassay was first demonstrated an principle using monoclonal antibodies raised against human IL-2 in 1983, by Smith et al., (J. Immunol. 131:1808–1815 (1983). Because the DMS-1, DS-2 and DMS-3 MAbs recognize different epitopes of the IL-2 molecule, it was conceptulized that a sandwich ELISA constructed with two different Abs could result in a rapid, sensitive and specific assay for immunoreactive IL-2. An ELISA based method for the quantitation of human IL-2 was first reported in 1984 by Gehman and Robb using a murine monoclonal antibody and a rabbit polyvalent antibody—similar to the methodology employed here. See Gehman, L. and Robb, R., J. Immunol. Meth. 74:39–47 (1984). This IL-2 ELISA was shown to react with natural glycosylated and recombinant non-glycosylated human IL2s. However, the sensitivity as reported was approximately 100 fold less than the bioassay. Recently, a quantitative radioimmunoassay (RIA) developed at Scripps Clinic was reported to approach the sensitivity of the bioassay, again using a mouse monoclonal antibody and a rabbit polyvalent (Cardenas, J. et al., J. Immunol. Meth. 89:181–189 (1986)). But the RIA was found to be 2014 50 fold less sensitive in detecting natural IL-2 as compared to rIL-2, and was inhibited approximately five-fold by the addition of human serum or plasma.

The most recent development has been the report of a sensitive and reproducible assay in 1986 by Smith et al. using two IL-2 reactive MAbs-, DMS-1 and DMS-5 (Budd, R. and Smith, K. Bio/Technology 4:983–986 (1986)). The immunoassay was reported to detect both human and murine IL-2 to a sensitivity of 150 pg/ml and was experimentally configured for both radioisotopic and enzymatic detection. Since both MAbs are raised against the same species, a third anti-murine Ab cannot be used in the amplification step. Instead, the second MAb is biotinylated and an avidin-alkalane phosphatase step is used to amplify. Unfortunately, the biotin-avidin system is known to be subject to a certain degree of non-specific binding with high background levels unless titered and incubated carefully.

IL-2R

The human immune system is composed of both specific and nonspecific mechanisms organized against infectious pathogens, malignancies, and transplanted foreign tissues. However, among these responses only T- and B-lymphocytes are capable of specifically recognizing foreign antigens and mounting an antigen-specific immune response. The activation of resting T-lymphocytes, involving the expression of the membrance IL-2 receptor (IL-2R) and the synthesis of IL-2 results in the growth and differentiation of human activated T-cells. This T-cell activation is initiated primarily by foreign antigens [examples are: viral and other infectious agents and allogeneic tissue antigens such as human leukocyte antigens (HLA) present on transplanted tissues] which are recognized in association with molecules of the major histocompatability complex (MHC). T-cell growth, proliferation and activation is governed by T-cell growth factor, now called interleukin-2 (IL-2). For IL-2 to exhibit its immunological effects, it must bind to a specific membrane glycoprotein receptor molecule, the IL-2 receptor (IL-2R), which is present in augmented numbers on the membranes of activated T-cells and other immunocompetent cells expressing this receptor molecule. The cell membrance IL-2R has been biochemically purified and is known to be a transmembrane glycoprotein with an apparent molecular mass of approximately 65,000 daltons, and approximately 55–58,000 daltons when de-glycosylated. This lymphokine-specific receptor binds IL-2 with two different binding co-efficients, depending on the presence of absence of a third related protein membrane component of the complex (the so-called Beta peptide). The mature processed IL-R contains 251 amino acids and has been extensively characterized both physiochemically and by recombinant DNA cloning.

Using two distinct murine monoclonal antibodies directed against two different epitopes expressed on the human IL-2R, Rubin et al. detected a soluble or released form of the molecule in normal serum and in culture supernatants of stimulated T-cells.

SUMMARY OF THE INVENTION

This invention pertains to a method of ascertaining the immune status of an individual particularly an allogeneic graft recipient by [and/or interleukin-2 measuring interleukin-2 (IL-2 receptor (IL-2R) levels in a biological fluid of an individual The method comprises determining the levels of IL-2 and/or IL-2R preferably by immunochemical means in a biological fluid of the individual and relating the values obtained to predetermined values as indicative of an abnormal condition or of a change in immune status. The information can be used in the monitoring and treatment of organ transplant recipients such as kidney and liver transplant recipients and other individuals undergoing immunosuppressive therapy such as patients with rheumatoid arthritis and systemic lupus erythematosis.

The measurement of IL-2 and IL-2R levels in blood, urine, bile, or other fluids makes possible the detection of organ rejection at least 2-5 days, and as many as 7-8 days, prior to its clinical manifestation. Prior to a rejection episode, IL-2 and IL-2R levels increase and persist at high levels throughout the episode. Thus the determination of IL-2 and IL-2R levels allow prediction of impending graft rejection.

IL-2 and IL-2R levels were found to be of great utility as a diagnostic and prognostic tool indicating generalized or localized acute immune system activation and would therefore allow earlier clinical evaluation to differentiate between infection and impending graft rejection. Heightened IL-2 levels detected in the blood or urine of transplant patients gives the clinician approximately 2-8 days advanced warning of heightened immune activation. This will enable the clinician to treat infection and rejection at an earlier stage than previously was possible, and so limit the damage done by either the infection or rejection episode. In addition, as it shows when the process has been successfully treated it will be able to accurately titrate the amount of treatment needed and so limit the amount of immunosuppression given. This is important as too much immunosuppression is known to cause life threatening infections and to have an increased incidence of malignancy.

In renal allograft recipients, monitoring IL-2 and IL-2R in the plasma and urine will detect both rejection and infection, both bacterial and viral, before any clinical manifestation.

In liver allograft recipients, monitoring IL-2 and IL-2R in the plasma and bile, as with renal allograft recipients, will detect both rejection and infection, both bacterial and viral, before any clinical manifestation.

IL-2 and IL-2R levels allows an accurate differential diagnosis of between cyclosporin toxicity and acute allograft rejection before either condition results in irreversible damage. With the increasing use of cyclosporin in all types or organ transplantation, the ability of monitoring IL-2 and IL-2R levels in plasma, urine bile and other bodily fluids to distinguish between cyclosporine toxicity and rejection is an extremely important clinical application, as distinguishing between cyclosporin toxicity and rejection is the most common problem facing transplant surgeons. The measurement of IL-2 and IL-2R levels in the cases of kidney dysfunction (rising creatinine levels for example, and in cases of hepatic dysfunction (rising bilirubin levels) allows for the correct differential diagnosis of cyclosporine toxicity (no IL-2 in blood, bile, or urine) or rejection (high urinary, bile or blood IL-2 levels).

Additionally, preoperative IL-2 and IL-2R levels show quite clearly that the higher the preoperative levels, the more likely the chance of a subsequent rejection episode and the postoperative period. This is of tremendous value for screening transplant candidates and transplanting them only when their IL-2 and IL-2R levels are optimal. In addition, we have shown that hemodialysis activates the immune system and may be detrimental prior to transplantation treatment, and may allow immunsuppressive modification of a patient's pretransplant regimen.

Viral illness will increase the plasma IL-2 and IL-2R levels and this will decrease to baseline levels when the infection has cleared. This also has tremendous clinical application in being able to detect both bacterial and viral illnesses earlier than previously possible and also in the ability to be able to tell when an illness has been successfully treated, and so limit the amount of treatment given. During CMV and during other acute infections, the presence of high IL-2 levels in the blood or urine can indicate whether the infection is systemic septicaemia or organ localized infection respectively.

DETAILED DESCRIPTION OF THE INVENTION

IL-2 levels have been found to be of utility as a diagnostic and prognostic tool indicating generalized and localized acute and chronic immune system activation. Early elevated IL-2 levels are detected in biological fluids of transplant patients approximately 2-8 days prior to an episode of acute rejection of the transplant. The high levels persist throughout the episode of rejection. Thus, measurement of IL-2 levels in biological fluids of transplant recipients provides clinicians with approximately 2-8 days advance warning of heightened immune activation and impending graft rejection. This allows the clinician to take appropriate early steps in treatment. Additional tests can also be performed in time to fully assess the situation. For example, immunosuppressive therapy can be adjusted to combat rejection. IL-2 or IL-2R levels also allow the clinician to monitor recovery from the transplant surgery or a rejection episode. Low or absent levels of IL-2 confirm a stable transplant and in rejection episodes and in the case of rejection, a return to low levels indicate recovery from a rejection episode.

Concomitant with the increase in IL-2 levels, IL-2R levels have also been found to increase approximately 2-8 days prior to the onset of an allograft rejection. Accordingly, IL-2R levels provide an additional indicator of impending graft rejection and a means for monitoring the status of an allograft patient.

Increased levels of IL-2 and IL-2R are found in cases of infection, particularly in viral CMV infection, regardless of whether it is localized to the transplanted organ or found systemically. However, these heightened IL-2 levels tend to be somewhat lower than those found during periods of acute allograft rejection, and urinary levels average lower. However, during CMV and during other acute infections, the presence of high IL-2 or IL-2R levels in the blood or urine can indicate whether the infection is systemic septicaemia or organ localized respectively. In the case of CMV infections, as with acute organ rejection, high IL-2 levels in the blood or urine appeared as early as eight days before clinically apparent evidence. This allows early intervention to prevent rejection or treat the infection.

IL-2 and IL-2R levels also allows a clinician to distinguish between rejection of an allograft and toxicity due to the immunosuppressive therapy which the patient is undergoing. In toxicity, IL-2 and IL-2R levels remain low where in rejection levels increase. This ability to distinguish can have profound effects on the choice of therapy and ultimate success of the transplantation procedure.

For example, in the cases of kidney dysfunction (rising creatinine levels for example) the measurement of IL-2 levels allows for the correct differential diagnosis of cyclosporine toxicity (no detectable IL-2 in blood or urine) or rejection (high urinary or blood IL-2 levels). This feature of the present invention represents a powerful diagnostic tool that is an immense improvement over the classical, ambiguous, and often "after the fact" renal cytology test currently used to differentiate cyclosporine toxicity from renal graft rejection.

Preoperative levels of IL-2 or IL-2R provide an indication of the likelihood of rejection of an allograft. It has been found that patients who have rejected an allograft have shown higher levels of IL-2 and IL-2R preoperatively than patients who have accepted grafts. Thus, higher levels of IL-2 or IL-2R preoperatively indicate a likelihood of rejection. Prospective recipients exhibiting high IL-2 levels can be subjected to immunosuppression or other therapy to reduce the IL-2 or IL-2R levels prior to the transplant. Low preoperative IL-2 and IL-2R indicate a high likelihood of success of the transplant and can help in appropriate scheduling of the procedure.

Measurement of IL-2 also allows the detection and diagnosis of autoimmune diseases which, like allograft rejection, are related to undesired activation of the body's immune system. In cases such as Rheumatoid Arthritis (RA), IL-2 measurement provides information affecting the prognosis, probable course and treatment of the patient with drugs such as methatexate. In cases such as Systemic Lupus Erythematosis (SLE), IL-2 measurement allows monitoring of the disease and also its immunsuppressive therapy with drugs such as cyclosporine.

The measurement and monitoring of IL-2 and IL-2R levels has clinical value with respect to the aforementioned diseases, such as SLE and RA, but is not limited to them. Other disorders wherein measurement of IL-2 levels may be of novel clinical utility includes Sjogren's syndrome, primary biliary cirrhosis, autoimmune insulin-dependent diabetes mellitus, membraneous glomerulonephritis, Wegener's granulomatosis, chronic active hepatitis, inflammatory bowel disease, autoimmune hemolytic anemia, immune thrombocytopenia, progressive systemic and multiple sclerosis, hemorrhagic cystitis, alopecia, scleroderma, allergic contact dermatitis, eczema, vasculitides, psoriasis and allergic conditions.

The method of this invention has several advantages. The procedure is non-invasive and allows early detection of an acute allograft so that successful immunosuppressive therapy can by instituted. In addition, it also allows early detection of infection (especially CMV infection) and appropriate early therapy can be instituted. Cyclosporine toxicity can be distinguished from acute rejection allowing appropriate choice of therapy. Because of early detection, lower doses and fewer combinations of drugs can be used in treatment with attendant reduction in adverse or toxic reactions.

Methods for measuring IL-2 and IL-2R levels

According to the method of this invention levels of IL-2 and IL-2R are measured in biological fluids of patients whose immune status is to be monitored. In renal transplant patients, for example, IL-2 and IL-2R levels can be determined in serum and in urine. In hepatic transplant patients levels in the bile can also be ascertained.

Any method for measuring IL-2 or IL-2R levels having appropriate sensitivity to distinguish between levels indicative of activated immune system and those indicative of an inactivated immune system can be used. Preferred methods of detection have a sensitivity of at least approximately 1 ng/ml for IL-2 and about 200 units/ml for IL-2R. (1000 units is the amount released or soluble IL-2R present in 1.0 ml of a reference preparation of supernatant from phytohemaglutinin stimulated peripheral blood lymphocytes obtained from T Cell Sciences, Inc., Cambridge, MA). Especially preferred assays are those having a sensitivity for IL-2 in the program range.

The preferred type of assays for measurement of IL-2 and IL-2R are immunochemical assays. This includes radioimmunoassay, radioimmunoprecipitation assay, any Western blot or immunoblot assay or other immunoassay using specific adn sensitive monocloal or polyclonal antibodies to IL-2 or IL-2R to quantitate these two soluble proteins involved is immune system activation. Solid phase immunometric assays of the sandwich type are most preferred. In general, these assays are performed by immobilizing a "capture" antibody on a solid phase such as a microplate or a bead. The solid phase is then contacted with a sample of the biological fluid in which the level of IL-2 or IL-2R is to be measured under conditions which allow the immobilized antibody to complex the IL-2 or IL-2R in the sample. The solid phase is then separated from the sample and incubated with a labeled antibody specific for IL-2 or IL-2R under conditions which allow the labeled antibody to bind the IL-2 or IL-2R associated with the solid phase. The antibody can be labeled with a radioisotope, an enzyme, a fluorescent molecule or other species which generates a detectable signal. After incubation with the labeled antibody the solid phase is separated and the amount of label associated with the solid phase is determined as an indication of the amount of IL-2 or IL-2R in the sample.

In a particularly preferred mode, an unlabeled second antibody is allowed to react with IL-2 or IL-2R associated with the solid phase and subsequently, a third labeled antibody directed against the second antibody is incubated with the solid phase. This permits amplification of the signal generated by the labeled antibody and consequently, improves sensitivity of the assay.

Kits for performing the IL-2 and IL-2assays are commercially available. These include InterTest-2 TM Genzyme Corp., Boston, MA and the Cellfree TM Interleakin-2 receptor test kit, T Cell Sciences, Inc., Cambrigde, MA).

This invention is illustrated further by the following exemplification.

Exemplification

Brief description of immunoassays utilized to measure IL-2 levels and soluble IL-2 receptor (IL-2R) levels.

IL-2 ELISA Methodology

Using a specific quantitative immunoassay based on the "dual antibody immunometric sandwich" principle, we have been able to detect as little as 0.05 unit/ml (50 programs) of IL-2 in culture supernatants, serum, plasma, urine, bile and other body fluids. The assay utilizes a monoclonal antibody (MAb) against human IL-2 (DMS-1, an $IgG_1$ kappa isotype) which recognizes only biologically active human or murine IL-2, both natural and recombinant forms, and has been extensively characterized. The DMS-1 MAb is specific for IL-2 and provides the means of capturing IL-2 in the wells of a polystyrene immunoplate or on polystyrene beads.

A high titer heteroantiserum against IL-2 was raised in New Zealand white rabbits to serve as second antibody for the IL-2 ELISA. Immune serum is pooled to prepare large lots of a purified, standardized anti-IL-2 preparation (2,000 mls of polyvalent IgG at 1.0 mg/ml). Sequential ammonium sulfate precipitation (45%) followed by Protein A-agarose affinity chromatography results in a greater than 95% pure preparation that binds to and neutralizes recombinant and natural human IL-2 with equal avidity.

The ELISA methodology is not only quite reproducible, with a coefficient of intrassay variation less than 10%, but yields results considerably faster (6–12 hours) than the bioassay. The method does not require preheating of serum samples and is sufficiently sensitive to measure IL-2 throughout the range encountered clinically from 0.05 units up to 2,000 units/ml (50 picograms/ml to 2.0 micrograms/ml). The linearity of the immunoassay (5 logs) is much greater than that of the bioassay (2 logs). A brief description of the methodology is described below. This methodology has been licensed to Genzyme Corporation and is marketed by them as the InterTest-2 TM, a fast and reproducible assay for the measurement of human IL-2.

The wells of a 96-well microtiter immunoplate coated with monoclonal antibody to IL-2 (DMS-1, 50 ug/ml) by incubating with a 50mM $Na_2CO_3$, 50 mM $NaHCO_3$ coating buffer, pH 9.6, for 16 hours at 37° C. Plates can be coated in advance and stored for up to 4 weeks if kept sealed and humidified at 4° C. Just prior to running the assay, a plate is washed four times with phosphate-buffered salines, pH 7.4, containing 0.2% Tween-20 (PBS-Tween). Negative controls and dilutions of rIL-2 standardized to the NIH reference (Biological Response Modifiers Program, BRMP) standard are placed in the first twelve wells, 100 ul per well, followed by test serum samples in duplicate in the remaining wells. The plate is then incubated at 37.C for six hours. With the IL-2 "capture step" complete, the plate is washed again the PBS-Tween and 100 ul of purified polyvalent rabbit IgG to IL-2 is added to each well (20 ug/ml in PBS-Tween), and allowed to incubate for one hour at 37° C. The plates are again washed and incubated with 100 ul of 1:3000 dilution of specific third antibody (goat anti-rabbit IgG, adsorbed to mouse Ig, conjugated with alkaline-phosphase, 0.5 mg/ml in 50 mM Tris buffered saline with 50 mg/ml BSA). After one hour, the plates are washed one last time and an enzyme substrate is added (for alkaline-phosphatase, 100 ul/well of 1.0 mg/ml para-nitrophenyl phosphate solution in 0.1 M glycine buffer, pH 10.4 containing 1.0 mM $MgCL_2$ and 0.1 mM $ZnCL_2$). The absorbance is then recorded with an ELISA reader at 405 nM. IL-2 concentration of the serum samples is determined by extrapolation from the standard curve.

IL-2 Receptor ELISA Methodology

The IL-2R test kit (Cellfree TM, IL-2 Receptor Test Kit, T-Cell Sciences, Cambridge, MA), used for these studies and the results presented in this application are based on a "dual antibody immunometric sandwich" ELISA similar to the one discussed for the detection of IL-2. It is capable of measuring IL-2R in serum, plasma, urine, bile and other biological fluids. First, one of the anti-IL-2R murine monoclonal antibodies is adsorbed onto the wells of a polystyrene immunoplate. IL-2R present in the sample or IL-2R standard is bound by the monoclonal antibody to the well and other molecules present art removed by washing with PBS-Tween and aspiration. A second monoclonal antibody to the IL-2R, directed against a different epitope on the IL-2R glycoprotein molecule and conjugated with the enzyme horseradish peroxidase, is added to the wells and allowed to bind to any captured IL-2R. After additional washings and aspiration, the substrate orthophenyldiamine (OPD) in citric acid buffer containing hydrogen peroxide is added to each well and allowed to develop. The resulting color change is directly proportional to the quantity of IL-2R in the sample and ii calculated by comparison with the IL-2R standard curve using linear regression analysis, after first stopping the enzymatic reaction with 12% $H_2SO_4$ and measuring the absorbance at 490 nM on an ELISA reader. The standard curve is generated with four dilutions of a known preparation of IL-2R present in PHA-stimulated human peripheral blood mononuclear cell supernatants, or with recombinant purified human IL-2R.

Measurement of IL-2 and IL-2R in body fluids as a means of monitoring immune activation associated with organ transplants.

Serial daily plasma and urinary Interleukin-2 and Interleukin-2R levels were measured in normal individuals and renal allograft recipients and compared to urinary cytology. This data is summarized in Table 1. Criteria for assigning patients into the following categories as detailed in Table 1 are:

(1) Normals—Individuals who have never has an organ transplant, are not on immunosuppressive therapy, and have no evidence of infection.

(2) Stable transplants—(Stable Tx)—patients who have had a renal allograft and have a stable creatinine level, show no evidence of bacterial or viral agents, and demonstrate no symptoms of cyclosporine toxicity.

(3) Acute rejection—renal allograft recipients who have a renal biopsy positive for rejection or have the clinical symptoms of rejection. In addition, confirmation of acute rejection by examining urine cytology, included increased exfoliation of collecting duct cells, lymphocyturia, and the binding of anti-human globulin by exfoliation renal cells indicating extensive tissue damage resulting from an active, ongoing cellular and humoral immune response to the grafted tissue resulting in the deposition and exfoliation of immune complexes detectable in the urine.

(4) Cyclosporine toxicity—Patients who had marked symptoms or signs of CsA toxicity and in addition whose serum creatinine reduced upon cessation of CsA dosage. CsA toxicity was also confirmed by cytology which included increased exfoliation of renal tubular cells demonstrating nuclear pyknosis and cellular vacuolization but no binding of anti-human globulin.

(5) Viral Infection—Viral infection was due primarily to cytomegalovirus (CMV) infection. CMV infection was diagnosed by clinical criteria, positive urine cytology for CMV, and positive blood and/or urine cultures.

Normal urinary and plasma IL-2 levels were established by measuring plasma IL-2 in 30 normal individuals and urinary IL-2 in 34 early morning urine specimens from normal people. The mean plasma IL-2 level was 1.3 ng/ml. No IL-2 was detectable in the urine of normal individuals.

In 73 stable renal allografts (245 plasma samples, 263 urine samples) the mean plasma IL-2 was 0.8 ng/ml with no detectable urinary IL-2. This lower mean plasma IL-2 level when compared to normal individuals was significant at $p<.01$ and is due to the immunosuppressive therapy these patients are receiving. It also shows quite clearly that a stable renal allograft should have no IL-2 detectable in their urine.

In 28 patients with 39 documented acute rejection episodes, mean plasma IL-2 level was 77.6 ng/ml. In 37 patients who had 49 documented episodes of acute rejection, the mean urinary IL-2 was 26.3 ng/ml. These results are highly significant when compared to both the stable transplant group and normal individuals ($p<0.0005$). We have since found that normal people who have not had a renal allograft and who are not on immunosuppressive therapy have undetectable IL-2 in their urine despite a wide variety of urinary tract pathologies. This indicates that the IL-2 which we are measuring in acute rejection is being produced locally in the transplanted kidney and is not coming from their natural kidney. Another very important point to note is that urinary IL-2 becomes detectable three to eight days prior to any clinical evidence of rejection. In uncomplicated rejection the plasma IL-2 shows exactly the same trend as the urinary IL-2 in that a detectable rise will occur at the same time that urinary IL-2 becomes detectable.

In both viral and bacterial infections localized to the transplanted kidney, urinary IL-2 again becomes detectable two to eight days prior to clinical evidence of infection. In systemic infections not involving the transplanted kidney, changes in the plasma IL-2 reflect the systemic illness but no IL-2 is detectable in the urine. In systemic infections involving the transplanted kidney as well, such as in CMV septicemia where both blood cultures and urine cultures are positive for the virus, IL-2 is detectable in both the plasma and the urine. When either the systemic infection or the infection localized in the transplanted kidney is cleared, IL-2 becomes undetectable in the plasma and urine.

In 18 documented cases of CsA toxicity where the serum creatinine improved on reduction of the CsA dose, no IL-2 was detectable in either the plasma or the urine. This is extremely important in comparison to the high IL-2 level obtained in the acute rejection group and provides a means for distinguishing between the two. The mean plasma IL-2R in 9 patients with documented CMV septicaemia was 1053.5 units/ml, with a mean urinary IL-2R of 200.9 units/ml. In 18 patients with CsA toxicity, the mean plasma IL-2R was 402.3 units/ml with a urinary IL-2R of 50.0 units/ml. In systemic infections, both bacterial and viral (other than CMV), the mean plasma IL-2R was 1503.9 units/ml. These results are highly significant ($p<0.005$) when compared to the acute rejection group. These results are summarized in Tables 1 and 2.

In addition to monitoring IL-2 levels, plasma IL-2 receptor (IL-2R) levels in 26 normal people were measured and a mean level of 318.4 units/ml found. The mean urinary IL-2R in 24 normal people was found to be 170.2 units/ml. In 30 stable renal allograft recipients the mean plasma IL-2R level was found to be 382.6 units/ml and the mean urinary IL-2R level 140.3 units/ml. In 18 patients who had documented acute rejection episodes, the mean plasma IL-2R was 1480.0 units/ml, whereas the mean urinary IL-2R was 649.4 units/ml in ten patients. When compared to the normal values given above and also the values obtained in the stable transplant group, these very elevated IL-2R levels are highly significant ($p<0.005$) as an indicator of immune activation and impending rejection.

In patients suffering from chronic rejection there is also a very significant elevation in their plasma and urinary IL-2 and IL-2R. These results are also summarized in Table 1. In addition, both urinary and blood levels rise as the chronic rejection increases, showing that monitoring lymphokine levels such as IL-2 and IL-2R correlate with the clinical degree of rejection. This will be extremely useful in the clinical management of these patients.

In renal allograft recipients both bacterial and viral urinary tract infections other than CMV will cause an elevation in the urinary IL-2 and IL-2R predominantly which will precede the clinical evidence of infection by 3-8 days. Urinary IL-2 and IL-2R return to baseline levels when the infection is cleared. This shows the value of monitoring lymphokine levels and the early detection of urinary tract infections other than CMV, both bacterial and viral and in the ability to show when the infection has cleared.

In addition, serial urinary cytology on early morning urine specimens correlated directly with the changes in plasma IL-2 and IL-2R, and urinary IL-2 and IL-2R. The rejection pattern was observed in all cases of acute rejection, the CsA toxicity two to three days after changes in the plasma or urinary IL-2.

Preoperative Plasma IL-2 and IL-2R Levels as Predictors of Subsequent Rejection Preoperative plasma IL-2 and IL-2R levels were measured prospectively on 19 renal allograft recipients who subsequently had an acute rejection episode, and in patients who underwent hemodialysis prior to transplant and compared to 25 renal allograft recipients who did not suffer an acute rejection episode. These results are summarized in Table 3 and show that the pre-operative plasma IL-2 levels in patients who subsequently suffer an acute rejection episode are significantly greater than in those patients who do not. In addition, plasma IL-2R levels were measured in 18 patients who subsequently suffered an acute rejection episode and compared to 17 patients who did not suffer an acute rejection episode. These results are also summarized in Table 3. This indicates that the higher. the pre-operative level of IL-2 and IL-2R, the more likely that one could predict a subsequent acute rejection episode. This would be extremely important in the clinical management of renal allograft recipients.

The mean plasma IL-2 levels were measured in 23 patients who had undergone haemodialysis prior to transplantation and compared to levels found in normal people and in stable renal allograft recipients. There is a very significant elevation in plasma IL-2 levels in patients who had undergone haemodialysis prior to transplantation. It may be that haemodialysis in some way triggers immune activation and increases the likelihood of subsequent rejection in the post-operative period.

IL-2 was measured in 18 liver allograft recipients (a total of 50 urinary and plasma determinations). Plasma IL-2 measured a mean of 48.4±11.5 while urinary IL-2 measured a mean of zero. Given these results, it would be expected that bile specimens would give an accurate and specific measurement of immune activation locally in the transplanted liver, and in fact, in every documented case of liver allograft rejection where IL-2 in the bile was measured, it correlated with serum bilirubin levels and liver function tests giving indications of rejection 2-8 days prior to its clinical manifestation. Plasma and urinary IL-2R levels were also measured, at 1514.8±202.2 and 131.2±61.3 respectively, and indicate the same results and utility as discussed above for IL-2. The results show that IL-2 is not normally detectable in the urine of liver allograft recipients, which further indicates that the IL-2 that we are detecting in the urine of renal allograft recipients is a specific indicator of the function of the transplanted kidney and is being locally produced by the transplanted kidney.

Examples of Acute Rejection

Example 1: J. L.

Figure 1:
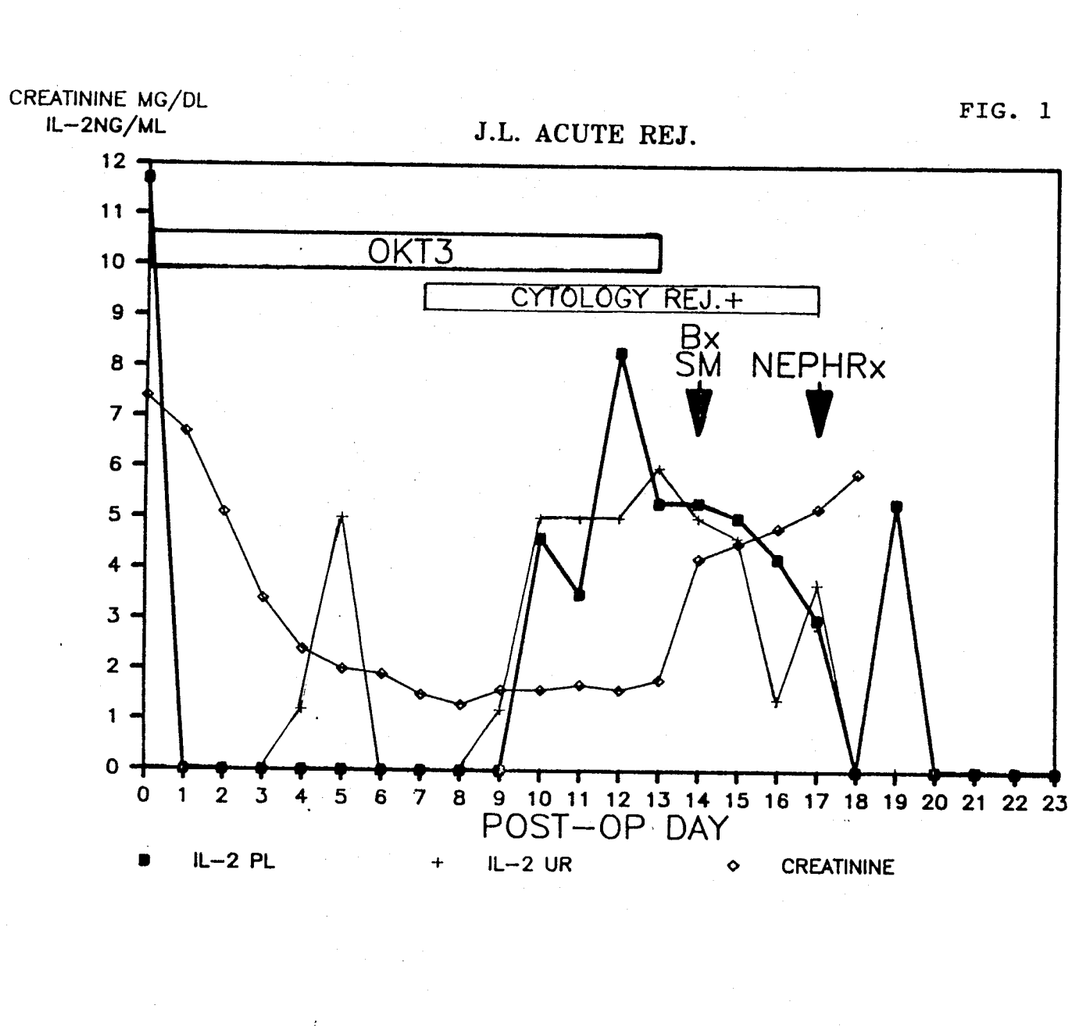
FIG. 1 shows the postoperative plasma creatinine levels, plasma IL-2 levels and urinary IL-2 levels of a renal transplant recipient (J. L.) who experienced an episode of acute rejection.

Despite having prophylactic OKT3 anti-rejection therapy (5 mg I.V. daily for fourteen days), this patient had an acute rejection episode which was clinically recognized at Day 15 post-operative when his plasma creatinine rose from 1.4 to 3.4, as shown in FIG. 1. On the same day, a kidney biopsy was performed which showed acute rejection and anti-rejection therapy started (solumedrol, an immunosupressive steroid, 1 gram daily for three days). Unfortunately, this rejection was unresponsive to solumedrol and necessitated a transplant nephrectomy on Day 17 post-operative from which he made an uneventful recovery. His urinary IL-2 shows two distinct peaks; the first at Days 4-6 post-operative, and then a larger sustained peak at Day 9, returning to zero only when the transplanted kidney was removed and remaining at zero in the five days following his transplant nephrectomy. Plasma IL-2 levels show a dramatic rise from Day 10 post-operative which then falls to zero following nephrectomy with a second peak at Day 19.

This second peak is probably due to the acute inflammation generated by the transplant nephrectomy. These results indicate that there was a rejection episode starting on Day 9 post-operative. By measuring urinary and plasma IL-2 we detected these rejection episodes eight days and five days prior to any clinical criteria and three days prior to his urinary cytology becoming positive for rejection. Also of note is the fact that the pre-operative plasma IL-2 was significantly raised above normal at 11.5 ng/ml and we have subsequently found that in patients who have detectable pre-op levels of plasma IL-2 there is a much increased incidence of an acute rejection episode following transplantation. The fact that the urinary IL-2 returned to zero the day following nephrectomy indicates that in kidney transplant patients, urinary IL-2 is a direct assessment of the transplanted organ.

Figure 2:
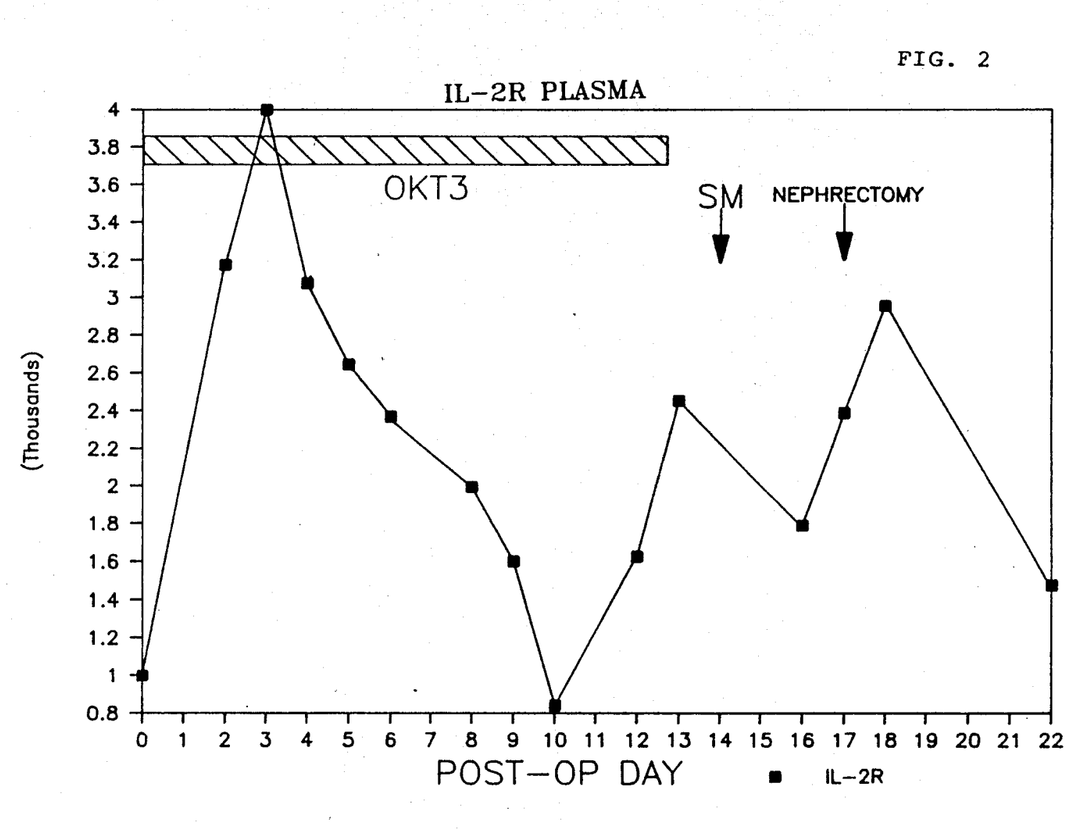
FIG. 2 shows the postoperative plasma IL-2R for the same patient (J. L.).

FIG. 2 shows this same patient's plasma IL-2R (soluble) levels during the same clinical time course and shows a dramatic rise on post-operative Day 2 falling to a subsequent baseline level on post-operative Day 10. This dramatic rise is due to monoclonal OKT3 prophylactic therapy causing T-cell damage. The second subsequent rise is due to the acute rejection episode and parallels the changes seen with plasma IL-2 returning to near baseline levels when the patient leaves hospital on Day 22. Given the relationship between IL-2 and its receptor, the observed results are expected, as both proteins indicative of heightened T-cell activation (IL-2 and its specific soluble glycoprotein receptor) return to normal levels as the rejection episode is controlled with clinical immunsuppressive therapy.

Example 2: ES.

Figure 3:
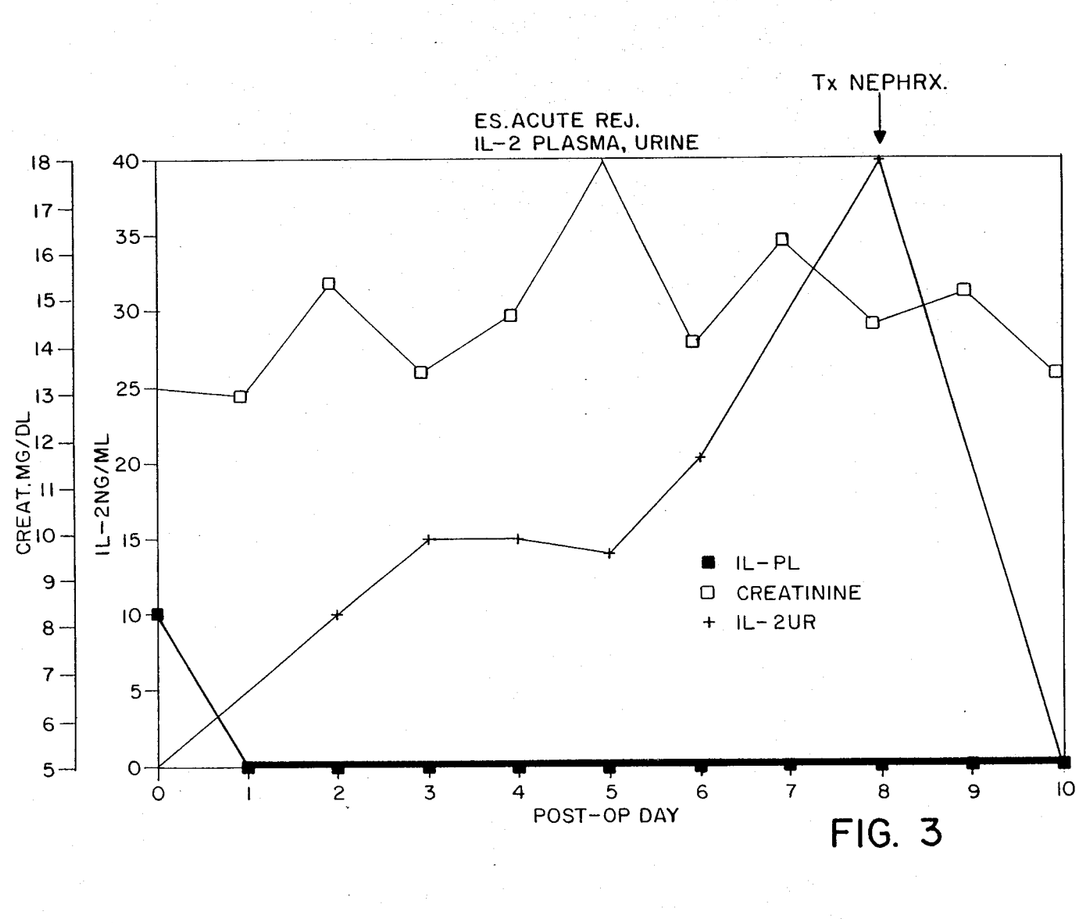
FIG. 3 shows postoperative plasma creatinine levels, plasma IL-2 levels and urinary IL-2 levels of a renal transplant recipient (E. S.) who experienced an episode of acute rejection.

This patient shows exactly what you don't want to see when monitoring the urine of kidney allograft recipients. Urinary IL-2 (FIG. 3) rises dramatically from the time he has his transplant, reaching a peak at Day 8 post-operative when he receives a transplant nephrectomy. As with Example 1, his urinary IL-2 returns to zero following his nephrectomy, again indicating that urinary IL-2 is a direct monitor of the transplanted organ. This patient's plasma IL-2 is undetectable during his postoperative course showing that urinary IL-2 is much more specific than plasma IL-2 in the monitoring of kidney allografts. However as in Example 1, he has measurable plasma IL-2 pre-operatively again indicating that he has an increased risk of rejection following transplantation.

Example 3: JB

Figure 4:
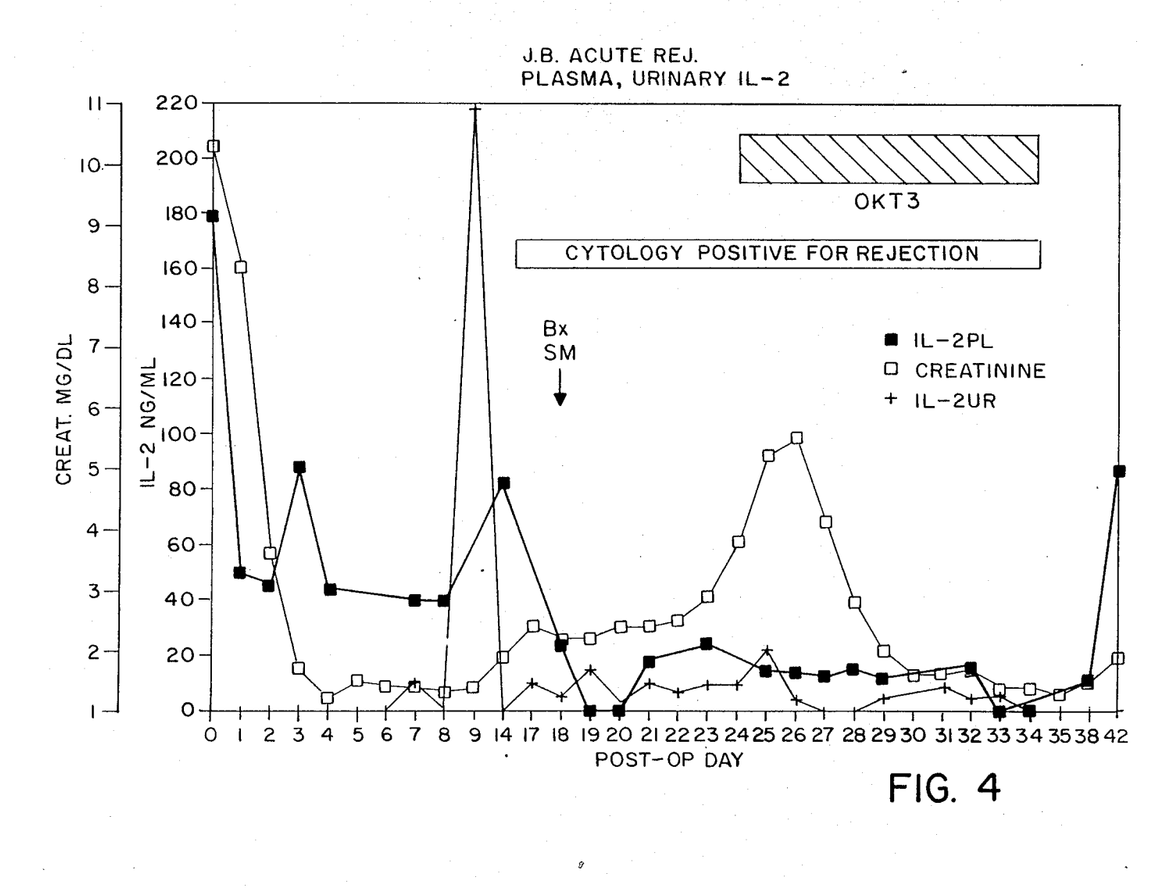
FIG. 4 shows postoperative serum creatinine levels, plasma IL-2 levels, and urine IL-2levels of a renal transplant recipients (J. B.) who experienced an episode of acute rejection.

This patient shows a rejection episode at Day 17 which required solumedrol (1 gram×five days) and a second steroid resistance rejection at Day 24 which required OKT3 (5mg I.V. daily for 10 days) before the creatinine returned to baseline levels. Urinary IL-2 levels shows a dramatic rise on Day 9 post-operative, eight days prior to clinical evidence of rejection and seven days prior to her cytology becoming positive for rejection. Only when the rejection episode is successfully treated does IL-2 disappear from this patient's urine on Day 34 post-operative. As in the previous example, this patient has a high preoperative IL-2 level, indicative that there is an increased risk of rejection in the post op period. If this patient had been treated when her urinary IL-2 became positive on Day 9, instead of waiting until she had clinical evidence of rejection on Day 17, the rejection episode may not have become so well established nor been so severe and may have required much less anti-rejection therapy and the dangers that entails. In the transplant unit where these patients were studied, the trend has been to try and treat rejection episodes at an earlier stage to limit the severity of the rejection episode and the amount of anti-rejection therapy given.

Examples of Viral Infection

Example 1: C.T

Figure 5:
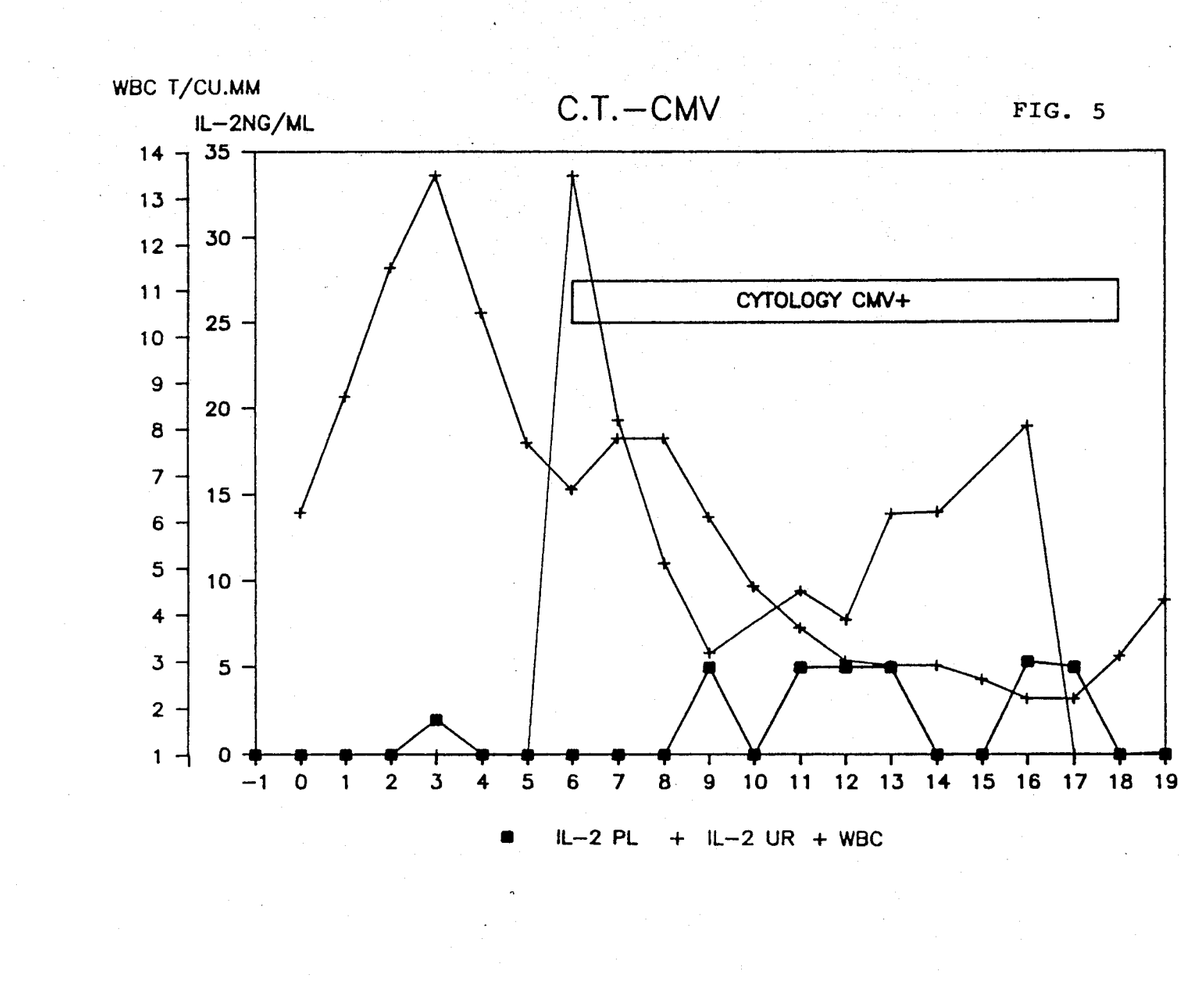
FIG. 5 shows postoperative plasma and urinary IL-2 levels and white blood cell count of a renal transplant recipient (C. T.) who experienced CMV infection.

Cytomegalovirus (CMV) has been increasingly recognized as the scourge of transplant units. Not only does it cause life threatening infections to patients on immunosuppressive therapy, but its ability to precipitate a rejection episode is becoming increasingly documented. This kidney transplant patient (FIG. 5) shows the ability of monitoring urinary IL-2 and plasma IL-2 to detect this potentially life threatening pathogen. The urinary IL-2 rose dramatically on Day 6 post-operative, five days before clinical evidence of CMV infection became apparent (positive cytology for CMV, intermittent fevers, and a dramatic fall in the white cell count) and disappeared on Day 17 post-operative when his CMV infection cleared and his white cell count began to rise to normal levels.

Example 2: R.O.D

Figure 6:
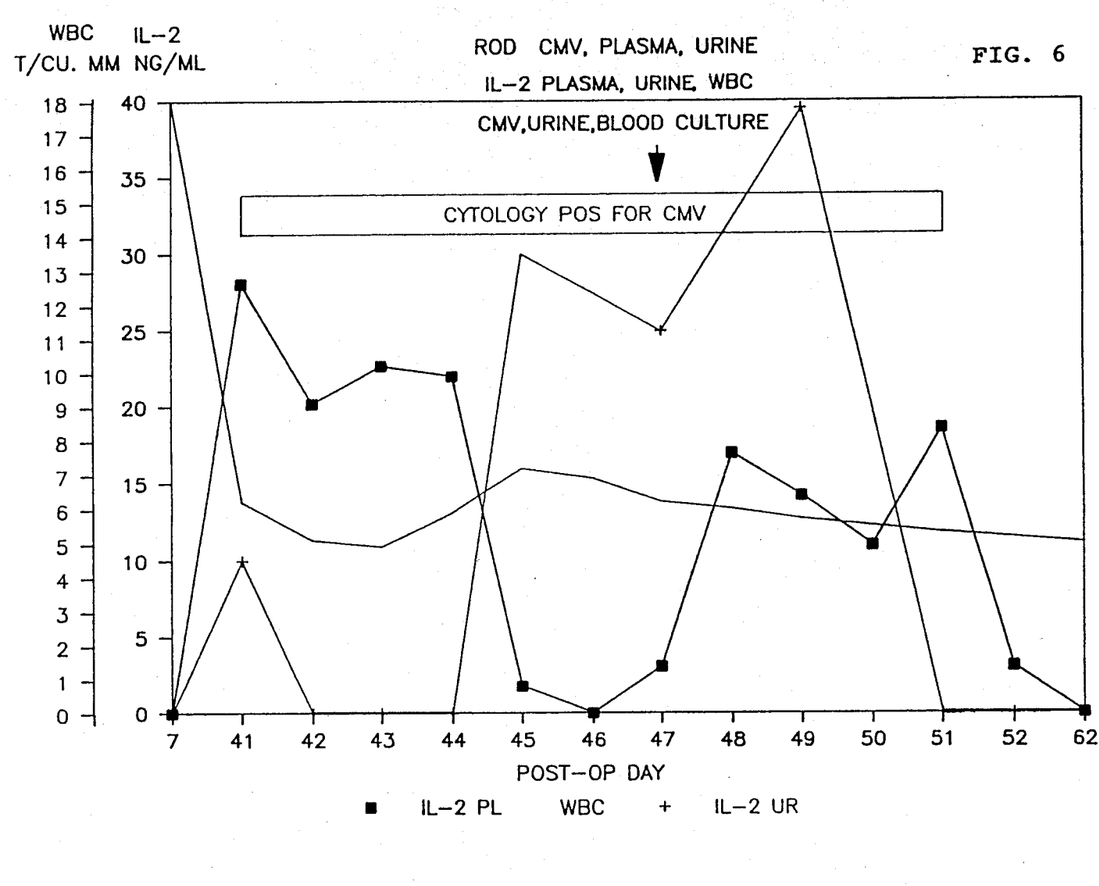
FIG. 6 shows postoperative plasma and urinary IL-2 levels and white blood cell count of a renal transplant recipient (R.O.D.) who experienced CMV infection.

This kidney transplant patient was admitted on postoperative Day 41 with CMV septicemia (positive urine, blood cultures for CMV; positive urine cytology for CMV; high intermittent fevers, abnormal organ function tests). The urinary IL-2 was elevated at the time of admission and remained intermittently elevated while she had CMV in her urine. As in the first example, IL-2 only disappeared from her urine when her CMV infection cleared. The plasma IL-2 remained elevated until her CMV septicemia cleared. The value of monitoring this patient's plasma and urinary IL-2 is in the ability to show when the infection disappeared, i.e. when the plasma and urinary IL-2 levels returned to zero.

Example of Cyclosporine Toxicity

Example 1: J.B

This patient was admitted 235 days after kidney transplantation with a rise in her creatinine from 1.4 to 2.7. The urinary and plasma IL-2 were both zero on admission and on subsequent serial samples. The differential diagnosis, as is often the case when presented with a rising creatinine and decreased renal function, is primarily between rejection and cyclosporine toxicity. As the admission IL-2 levels were zero and subsequently her urine cytology and cyclosporine levels were indicative of cyclosporine toxicity, this patient's cyclosporine dose was dropped from 350 mg to 300 mg, and then further reduced to 250 mg. This was associated with a fall in creatinine from 2.7 to 1.2. As in all cases of established cyclosporine toxicity (elevated cyclosporine levels, symptoms of toxicity, and a fall in serum creatinine when the cyclosporin was dropped) we have not been able to detect IL-2 either in the plasma or in the urine of these patients. This allows distinguishing toxicity clearly from active rejection and shows the value of monitoring all types of transplant recipients on cyclosporin as cyclosporin is becoming an increasingly used immunosupressive agent.

Liver allograft recipients

Example 1: Acute rejection

This patient who acutely rejected a liver allograft had markedly elevated plasma IL-2 levels at the time of this first rejection episode, necessitating a retransplant, i.e. a second liver allograft. Following this, she suffered a second rejection episode which coincided again with elevated plasma IL-2 levels. Only when her rejection had subsided did her plasma IL-2 levels become unmeasureable. Patient L.G. was admitted at the time of a severe rejection episode. Within a four day period, plasma IL-2 levels rose from 19.7 ng/ml to 97 ng/ml, while serum bilirubin concurrently rose to 20.8. At this point the patient received a second liver transplant due to the complete failure of the first graft. After three days, plasma IL-2 was significantly lower and bilirubin had diminished to 4.2 indicating clinical improvement. Three days later, rising IL-2 levels signalled a second severe rejection episode which was confirmed by serum bilirubin levels and liver function tests. Following successful immunosuppressive therapy, resulting in steady daily reduction in plasma IL-2 and serum bilirubin levels, within six weeks plasma IL-2 levels had fallen to zero and serum bilirubin had returned to a normal level of 1.4. The patient was—immunologically stable and discharged from the hospital with normal liver function. This shows clearly that as her liver function tests improve and as her rejection episodes resolve, so the plasma IL-2 decreases to unmeasurable levels.

Example 2: Acute rejection and subsequent infection

This patient suffered an acute rejection episode shortly after receiving her first liver allograft which necessitated a second transplant which functioned well. Following her second transplant she suffered a viral infection in her retransplanted liver but this subsequently cleared at around the time she was discharged, and when she was subsequently seen in the outpatients, her liver function tests were normal and clinically all parameters were excellent. These changes are reflected both in her plasma and biliary IL-2 levels. Patient F.T. was admitted to hospital undergoing severe liver allograft rejection, with a plasma IL-2 level on admission of 175 ng/ml, a bilirubin level of 12.4 and a bile IL-2 level of 25.9 ng/ml. On day 2 bile IL-2 increased to 59.9 ng/ml indicating severe, unresponsive rejection and the patient was retransplanted. Within 24 hours, plasma IL-2 had declined to 58.2 ng/ml, bilirubin was reduced to 4, and IL-2 was no longer detectable in the bile.

During the next month, the patient's plasma IL-2 levels steadily declined, as did serum bilirubin to near normal levels. During a one week period, the patient developed a transient viral infection from the transplanted liver. IL-2 levels in the plasma rose during this period to a high of 137 ng/ml. During the entire course, IL-2 was never detectable in the urine. As the viral septicemia resolved itself, plasma IL-2 levels fell to 11.3 and then 5.0 ng/ml with an extremely encouraging bilirubin of 1.1. Eight days later, with no IL-2 detectable in the urine or bile, and a stable bilirubin of 1.1, the patient was deemed to have normal liver function and was discharged.

Plasma and biliary IL-2 levels were very elevated prior to her rejection episode and also at the time of the subsequent viral infection. These levels both in bile and plasma only become unmeasurable when her clinical condition improves and she is free of rejection and infection. This shows the value of monitoring lymphokine levels such as IL-2 and IL-2R in the clinical management of these patients, and more importantly in their ability to predict impending rejection or infection analogous to what has been shown with renal allograft recipients.

Example 3: No rejection or infection, straight forward clinical course

This patient shows what happens to the plasma IL-2 levels in an uncomplicated liver allograft recipient.

Patient D.T. received a liver allograft. Plasma IL-2 levels were initially measured at 29.4 ng/ml postoperatively with a serum bilirubin level of 4.1. Over the next three weeks, plasma IL-2 levels feel successively to 15.1, 13.6, 10.7 and finally to zero ng/ml. During the same period, serum bilirubin levels fell successively to 3, 2, 1.4 and 1.1. The patient exhibited no complications, a straightforward clinical course and was discharged as an outpatient with normal liver function. This example confirms the relationship between plasma IL-2 levels and serum bilirubin levels as prognostic indicators in liver allograft recipients.

Viral infection in normal people

Plasma IL-2 levels were measured in eight patients who had documented acute viral illnesses. As shown in Table 2, these patients had a significantly elevated plasma IL-2 level when compared to normal people. This would be expected as IL-2 is known to be critical in the immune activation associated with viral illness. IL-2 levels return to normal when the viral illness subsided and this shows the ability of monitoring lymphokine levels such as IL-2 in recognizing an acute infection and in its ability to show when an infection has subsided. This will be of clinical value in limiting the amount of drug treatment given.

TABLE I

INTERLEUKIN 2 LEVELS IN PLASMA AND URINE, INTERLEUKIN 2 RECEPTOR LEVELS IN PLASMA AND URINE, AND URINE CYTOLOGY AS A MEANS OF MONITORING RENAL ALLOGRAFT RECIPIENTS

| | IL-2 NGIML Mean ± S.E. | | IL-2 A UNITSIML Mean ± S.E. | | |
|---|---|---|---|---|---|
| | PLASMA | URINE | PLASMA | URINE | CYTOLOGY |
| Normals | 1.3 ± 0.5 (n = 30) | 0 (n = 34) | 318.4 ± 21.9 (n = 26) | 170.2 ± 33.6 (n = 24) | — |
| Stable Tx | 0.8 ± 0.2 (n = 73, s = 245) | 0 (n = 73, s = 263) | 382.6 ± 19.8 (n = 30, s = 95) | 140.3 ± 22.7 (n = 30, s = 49) | — |
| Acute Rejection | 77.6 ± 24.9 (n = 28; nl, s = 39) | 26.3 ± 4.3 (n = 37; nl, s = 49) | 1480.0 ± 159.7 (n = 18; nl, s = 24) | 649.4 ± 182.2 (n = 10; nl, s = 13) | Acute Rejection Pattern |
| Chronic Rejection | 163.3 ± 42.2 (n = 7, nl = 8, s = 21) | 23.6 ± 5.0 (n = 7, nl = 8, s = 32) | 652.9 ± 121.2 (n = 7, nl = 7, s = 7) | 121.5 ± 85.9 (n = 2, nl = 2, s = 2) | Chronic Rejection Pattern |
| CsA Toxicity | 0 (n = 18, s = 61) | 0 (n = 18, s = 60) | 402.3 ± 32.6 (n = 18, s = 36) | 50.0 ± 16.9 (n = 13, s = 17) | CsA Toxicity Pattern | n = No. Patients
nl = No. Rejection Episodes
s = Total No. Samples

TABLE II

INTERLEUKIN 2 LEVELS IN PLASMA AND URINE, INTERLEUKIN 2 RECEPTOR LEVELS IN PLASMA AND URINE, AND URINE CYTOLOGY IN CASES OF VIRAL AND BACTERIAL INFECTION IN RENAL ALLOGRAFT RECIPIENTS AND NORMAL PEOPLE

| | IL-2 NGIML Mean ± S.E. | | IL-2 A UNITSIML Mean ± S.E. | | |
|---|---|---|---|---|---|
| | PLASMA | URINE | PLASMA | URINE | CYTOLOGY |
| Viral Infections in Normals | 63.6 ± 38.7 (n, s, nl = 8) | 0 (n, s, nl = 8) | — | — | |
| CMV Septicaemia | 21.6 ± 4.1 (n, nl = 9, s = 50) | 18.9 ± 3.2 (n, nl = 9, s = 34) | 1464.0 ±0 136.7 (n, nl = 9, s = 38) | 359.1 ± 39.0 (n, nl = 9, s = 15) | Infection Pattern for CMV |
| Urinary CMV | 6.3 ± 2.0 (n, nl = 11; s = 30) | 15.7 ± 5.4 (n, nl = 11; s = 32) | 1053.5 ± 152.0 (n, nl = 8; s = 13) | 200.9 ± 166.5 (n, nl = 7; s = 7) | Infection Pattern for CMV |
| Urinary Infection other than CMV | 13.1 ± 4.1 (n, nl = 11; s = 20) | 29.7 ± 4.6 (n, nl = 11; s = 23) | 620.3 ± 106.2 (n, nl = 9; s = 12) | 180.9 ± 53.4 (n, nl = 9; s = 10) | Infection Pattern |
| Localized Infection (Bact. & Viral) | 8.1 ± 1.2 (n = 16, s = 69, nl = 19) | 0 (n = 16, s = 57, nl = 16) | 771.5 ± 92.8 (n = 13, s = 40, nl = 13) | — | — |
| Septicaemia | 18.5 ± 2.5 | 0 | 1503.9 ± 147.8 | — | — |

TABLE II-continued

INTERLEUKIN 2 LEVELS IN PLASMA AND URINE,
INTERLEUKIN 2 RECEPTOR LEVELS IN PLASMA AND URINE,
AND URINE CYTOLOGY IN CASES OF VIRAL AND BACTERIAL INFECTION
IN RENAL ALLOGRAFT RECIPIENTS AND NORMAL PEOPLE

| | IL-2 NG/ML Mean ± S.E. | | IL-2 A UNITS/ML Mean ± S.E. | | |
|---|---|---|---|---|---|
| | PLASMA | URINE | PLASMA | URINE | CYTOLOGY |
| (other than CMV) | (n = 10, n1 = 11, s = 25) | (n = 10, n1 = 11, s = 19) | (n = 10, n1 = 11, s = 18) | | | n = No. Patients
n1 = No. Infection Episodes
s = Total No. Samples

TABLE III

PRE-OPERATIVE PLASMA IL-2 AND IL-2R, URINARY IL-2
LEVELS IN RENAL ALLOGRAFT RECIPIENTS SUBSEQUENTLY
EXPERIENCING AN ACUTE REJECTION AND IN PATIENTS
RECEIVING HEMODIALYSIS PRIOR TO RENAL ALLOGRAFT

| | PLASMA IL-2 NG/ML MEAN ± S.E. | PLASMA IL-2 A UNITS/ML MEAN ± S.E. | URINARY IL-2 NG/ML MEAN ± S.E. |
|---|---|---|---|
| NORMALS | 1.3 ± 0.5 (n = 30) | 318.4 ± 21.9 (n = 26) | 0 (n = 34) |
| NON REJECTORS | 5.5 ± 2.2 (n = 25) | 770.1 ± 90.3 (n = 17) | 0 (n = 25) |
| REJECTORS | 63.9 ± 30.0 (n = 19) | 1225.8 ± 96.4 (n = 18) | 0 (n = 19) |
| HEMODIALYSIS | 48.5 ± 25.3 (n = 23) | 975.2 ± 107.8 (n = 20) | 0 (n = 23) | n = No. Patients

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of determining the status of an allograft recipient comprising measuring IL-2 levels in a biological fluid taken from the recipient after receipt of the allograft and comparing the levels obtained to predetermined levels as an indication of acceptability of the allograft.

2. A method of claim 1, wherein the allograft is a kidney or liver.

3. A method of claim 1, wherein the IL-2 levels are measured daily after receipt of the allograft.

4. A method of claim 1, wherein the IL-2 levels are measured by immunochemical means.

5. A method of claim 4, wherein the immunochemical means comprise a solid phase sandwich immunoassay.

6. A method of claim 1, wherein the biological fluid is serum, plasma, urine, or bile.

7. A method of monitoring an allograft recipient comprising measuring IL-2 levels in a biological fluird taken from the recipient postoperatively on a periodic basis and comparing the levels obtained to predetermined levels as an indicator of stability, or impending rejection, of the allograft.

8. A method of claim 7, wherein the allograft is a kidney or liver transplant.

9. A method of claim 7, wherein the IL-2 levels are measured daily after receipt of the graft.

10. A method of claim 7, wherein the biological fluid is serum, plasma, urine or bile.

11. A method of claim 7, wherein the IL-2 is measured by immunochemical means.

12. A method of claim 11, wherein the immunochemical means is a solid phase immunometric assay.

13. A method of differentiating rejection of an allograft or viral infection from toxicity to immunosuppressive therapy in an allograft recipient, comprising measuring the levels of IL-2 in a biological fluid taken from the allograft recipient postoperatively and comparing the levels to predetermined levels to differentiate rejection of an allograft or viral infection from toxicity to immunosuppressive therapy in the allograft receipt.

14. A method of claim 13, wherein the allograft is a renal or hepatic transplant.

15. A method of claim 13, wherein the biological fluid is serum, plasma, urine or bile.

16. A method of claim 13, wherein the IL-2 levels are measured by immunochemical means.

17. A method of claim 16, wherein the immunochemical means comprises a solid phase immunometric assay.

18. A method of claim 13, wherein the immunosuppressive drug is cyclosporine.

19. A method of detecting infection or recovery therefrom in an individual, comprising measuring IL-2 levels in a biological fluid of the individual and comparing the levels obtained to predetermined levels as indicative of systemic or localized infection or recovery from infection.

20. A method of claim 19, wherein the individual is a recipient of an allograft and the infection which is detected is due to CMV.

21. A method of predicting acceptance or rejection of an allograft by a prospective allograft recipient comprising measuring preoperative IL-2 levels in a biological fluid of the prospective recipient and relating the levels obtained to predetermined levels as indicative of acceptance or rejection of the allograft.

22. A method of differentiating viral infection or rejection of a renal or hepatic allograft from toxicity to cyclosporine therapy, comprising measuring the level of IL-2 in a biological fluid taken from the allograft recipient undergoing cyclosporine therapy postoperatively and comparing the level to a predetermined level to differentiate rejection of the allograft or viral infection from cyclosporine toxicity in the recipient.

* * * * *

UNITED STATES PATENT AND TRADEMARK OFFICE
CERTIFICATE OF CORRECTION

PATENT NO.  : 4,959,302

DATED       : September 25, 1990

INVENTOR(S) : Andrew J. Cornaby and Roy A. Dempsey

It is certified that error appears in the above-identified patent and that said Letters Patent is hereby corrected as shown below:

Col. 22, Claim 13, line 35, change "receipt" to ---recipient---

Signed and Sealed this

Tenth Day of December, 1991

Attest:

HARRY F. MANBECK, JR.

*Attesting Officer*      *Commissioner of Patents and Trademarks*